United States Patent [19]

Riedl et al.

[11] Patent Number: 5,882,904

[45] Date of Patent: Mar. 16, 1999

[54] *THERMOCOCCUS BAROSSII* DNA POLYMERASE MUTANTS

[75] Inventors: William A. Riedl, Cedarburg; Susan J. Fly, Brookfield; Barbara F. Kaboord; Steven H. Nye, both of Mequon; Eve Y. Ting, Brookfield, all of Wis.

[73] Assignee: Amersham Pharmacia Biotech Inc.

[21] Appl. No.: 906,925

[22] Filed: Aug. 4, 1997

[51] Int. Cl.$^6$ .............................. C12N 9/12; C12P 19/34
[52] U.S. Cl. .......................................... 435/91.2; 435/194
[58] Field of Search ..................................... 435/194, 91.2

[56] References Cited

U.S. PATENT DOCUMENTS

| | | | |
|---|---|---|---|
| 5,322,785 | 6/1994 | Comb et al. | 435/194 |
| 5,489,523 | 2/1996 | Mathur | 435/194 |
| 5,602,011 | 2/1997 | Luhm et al. | 435/91.2 |

FOREIGN PATENT DOCUMENTS

| | | |
|---|---|---|
| 0 455 430 A2 | 4/1991 | European Pat. Off. . |
| 0 547 359 A1 | 11/1992 | European Pat. Off. . |
| 0 655 506 A1 | 11/1994 | European Pat. Off. . |
| 0 727 496 A2 | 8/1996 | European Pat. Off. . |

OTHER PUBLICATIONS

Z. Guo, et al., "Direct fluorescence analysis of genetic polymorphisms by hybridization with oligonucleotide arrays on glass supports," *Nucl. Acids Res.* 22(24):5456–5465, 1994.

T.T. Nikoforov, et al., "Genetic Bit Analysis: a solid phase method for typing single nucleotide polymorphisms," *Nucl. Acids. Res.* 22(20):4167–4175, 1994.

*Primary Examiner*—Keith D. Hendricks
*Attorney, Agent, or Firm*—Quarles & Brady LLP

[57] ABSTRACT

A *Thermococcus barosii* DNA polymerase with reduced 3'-5' exonuclease activity is disclosed. Additionally disclosed is a *Thermococcus barosii* DNA polymerase with increased ability to incorporate ribonucleotides and dideoxynucleotides.

8 Claims, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Phe  Asp  Ile  Glu  Thr
    1                          5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Phe  Ala  Ile  Ala  Thr
1                    5
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Lys  Ile  Leu  Ala  Asn  Ser  Phe  Tyr
1                    5
```

( 2 ) INFORMATION FOR SEQ ID NO:4:

( i ) SEQUENCE CHARACTERISTICS:
        ( A ) LENGTH: 778 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met  Ile  Leu  Asp  Val  Asp  Tyr  Ile  Thr  Glu  Asp  Gly  Lys  Pro  Val  Ile
1                    5                        10                       15

Arg  Val  Phe  Lys  Lys  Asp  Lys  Gly  Glu  Phe  Lys  Ile  Glu  Tyr  Asp  Arg
                20                       25                       30

Glu  Phe  Glu  Pro  Tyr  Ile  Tyr  Ala  Leu  Leu  Arg  Asp  Asp  Ser  Ala  Ile
          35                       40                       45

Glu  Glu  Ile  Glu  Lys  Ile  Thr  Ala  Glu  Arg  His  Gly  Lys  Val  Val  Lys
     50                       55                       60

Val  Lys  Arg  Ala  Glu  Lys  Val  Lys  Lys  Phe  Leu  Gly  Arg  Ser  Val
65                            70                  75                       80

Glu  Val  Trp  Val  Leu  Tyr  Phe  Thr  His  Pro  Gln  Asp  Val  Pro  Ala  Ile
                    85                       90                       95

Arg  Asp  Lys  Ile  Arg  Lys  His  Pro  Ala  Val  Ile  Asp  Ile  Tyr  Glu  Tyr
               100                      105                      110

Asp  Ile  Pro  Phe  Ala  Lys  Arg  Tyr  Leu  Ile  Asp  Lys  Gly  Leu  Val  Pro
          115                      120                      125

Met  Glu  Gly  Asp  Glu  Glu  Leu  Lys  Leu  Met  Ser  Phe  Asp  Ile  Glu  Thr
     130                      135                      140

Leu  Tyr  His  Glu  Gly  Glu  Glu  Phe  Gly  Thr  Gly  Pro  Ile  Leu  Met  Ile
145                      150                      155                      160

Ser  Tyr  Ala  Asp  Glu  Ser  Glu  Ala  Arg  Val  Ile  Thr  Trp  Lys  Lys  Ile
               165                      170                      175

Asp  Leu  Pro  Tyr  Val  Asp  Val  Val  Ser  Thr  Glu  Lys  Glu  Met  Ile  Lys
```

-continued

```
                    180                         185                          190
     Arg  Phe  Leu  Lys  Val  Val  Lys  Glu  Lys  Asp  Pro  Asp  Val  Leu  Ile  Thr
               195                      200                     205

Tyr  Asn  Gly  Asp  Asn  Phe  Asp  Phe  Ala  Tyr  Leu  Lys  Lys  Arg  Cys  Glu
          210                      215                     220

Lys  Leu  Gly  Val  Ser  Phe  Thr  Leu  Gly  Arg  Asp  Gly  Ser  Glu  Pro  Lys
     225                     230                     235                          240

Ile  Gln  Arg  Met  Gly  Asp  Arg  Phe  Ala  Val  Glu  Val  Lys  Gly  Arg  Ile
                    245                     250                          255

His  Phe  Asp  Leu  Tyr  Pro  Val  Ile  Arg  Arg  Thr  Ile  Asn  Leu  Pro  Thr
                    260                     265                     270

Tyr  Thr  Leu  Glu  Ala  Val  Tyr  Glu  Ala  Val  Phe  Gly  Lys  Pro  Lys  Glu
               275                     280                     285

Lys  Val  Tyr  Ala  Glu  Glu  Ile  Ala  Thr  Ala  Trp  Glu  Thr  Gly  Glu  Gly
          290                     295                     300

Leu  Glu  Arg  Val  Ala  Arg  Tyr  Ser  Met  Glu  Asp  Ala  Arg  Val  Thr  Tyr
     305                     310                     315                          320

Glu  Leu  Gly  Arg  Glu  Phe  Phe  Pro  Met  Glu  Ala  Gln  Leu  Ser  Arg  Leu
                         325                     330                     335

Ile  Gly  Gln  Gly  Leu  Trp  Asp  Val  Ser  Arg  Ser  Thr  Gly  Asn  Leu
                    340                     345                     350

Val  Glu  Trp  Phe  Leu  Leu  Arg  Lys  Ala  Tyr  Glu  Arg  Asn  Glu  Leu  Ala
               355                     360                     365

Pro  Asn  Lys  Pro  Asp  Glu  Arg  Glu  Leu  Ala  Arg  Arg  Gly  Gly  Tyr
          370                     375                     380

Ala  Gly  Gly  Tyr  Val  Lys  Glu  Pro  Glu  Arg  Gly  Leu  Trp  Asp  Asn  Ile
     385                     390                     395                          400

Val  Tyr  Leu  Asp  Phe  Arg  Ser  Leu  Tyr  Pro  Ser  Ile  Ile  Ile  Thr  His
                    405                     410                     415

Asn  Val  Ser  Pro  Asp  Thr  Leu  Asn  Arg  Glu  Gly  Cys  Lys  Ser  Tyr  Asp
                    420                     425                     430

Val  Ala  Pro  Gln  Val  Gly  His  Lys  Phe  Cys  Lys  Asp  Phe  Pro  Gly  Phe
               435                     440                     445

Ile  Pro  Ser  Leu  Leu  Gly  Asn  Leu  Leu  Glu  Glu  Arg  Gln  Lys  Ile  Lys
          450                     455                     460

Arg  Lys  Met  Lys  Ala  Thr  Leu  Asp  Pro  Leu  Glu  Arg  Lys  Leu  Leu  Asp
     465                     470                     475                          480

Tyr  Arg  Gln  Arg  Ala  Ile  Lys  Ile  Leu  Ala  Asn  Ser  Phe  Tyr  Gly  Tyr
                    485                     490                          495

Tyr  Gly  Tyr  Ala  Arg  Ala  Arg  Trp  Tyr  Cys  Lys  Glu  Cys  Ala  Glu  Ser
                    500                     505                     510

Val  Thr  Ala  Trp  Gly  Arg  Glu  Tyr  Ile  Glu  Met  Val  Ile  Arg  Glu  Leu
               515                     520                     525

Glu  Glu  Lys  Phe  Gly  Phe  Lys  Val  Leu  Tyr  Ala  Asp  Thr  Asp  Gly  Leu
          530                     535                     540

His  Ala  Thr  Ile  Pro  Gly  Ala  Asp  Ala  Glu  Thr  Val  Lys  Lys  Lys  Ala
     545                     550                     555                          560

Met  Glu  Phe  Leu  Asn  Tyr  Ile  Asn  Pro  Lys  Leu  Pro  Gly  Leu  Leu  Glu
                    565                     570                     575

Leu  Glu  Tyr  Glu  Gly  Phe  Tyr  Val  Arg  Gly  Phe  Phe  Val  Thr  Lys  Lys
                    580                     585                     590

Lys  Tyr  Ala  Val  Ile  Asp  Glu  Glu  Gly  Lys  Ile  Thr  Thr  Arg  Gly  Leu
               595                     600                     605
```

|     |     |     |     |     |     |     |     |     |     |     |     |     |     |     |
| --- | --- | --- | --- | --- | --- | --- | --- | --- | --- | --- | --- | --- | --- | --- |
| Glu | Ile | Val | Arg | Arg | Asp | Trp | Ser | Glu | Ile | Ala | Lys | Glu | Thr | Gln | Ala |
|     | 610 |     |     |     |     | 615 |     |     |     | 620 |     |     |     |     |     |
| Arg | Val | Leu | Glu | Ala | Ile | Leu | Arg | His | Gly | Asp | Val | Glu | Glu | Ala | Val |
| 625 |     |     |     |     | 630 |     |     |     | 635 |     |     |     |     |     | 640 |
| Arg | Ile | Val | Lys | Glu | Val | Thr | Glu | Lys | Leu | Ser | Lys | Tyr | Glu | Val | Pro |
|     |     |     |     | 645 |     |     |     |     | 650 |     |     |     |     | 655 |     |
| Pro | Glu | Lys | Leu | Val | Ile | His | Glu | Gln | Ile | Thr | Arg | Glu | Leu | Lys | Asp |
|     |     |     | 660 |     |     |     |     | 665 |     |     |     |     | 670 |     |     |
| Tyr | Lys | Ala | Thr | Gly | Pro | His | Val | Ala | Ile | Ala | Lys | Arg | Leu | Ala | Ala |
|     |     | 675 |     |     |     |     | 680 |     |     |     |     | 685 |     |     |     |
| Arg | Gly | Ile | Lys | Ile | Arg | Pro | Gly | Thr | Val | Ile | Ser | Tyr | Ile | Val | Leu |
|     | 690 |     |     |     |     | 695 |     |     |     |     | 700 |     |     |     |     |
| Lys | Gly | Ser | Gly | Arg | Ile | Gly | Asp | Arg | Ala | Ile | Pro | Phe | Asp | Glu | Phe |
| 705 |     |     |     |     | 710 |     |     |     |     | 715 |     |     |     |     | 720 |
| Asp | Pro | Thr | Lys | His | Arg | Tyr | Asp | Ala | Asp | Tyr | Tyr | Ile | Glu | Asn | Gln |
|     |     |     |     | 725 |     |     |     |     | 730 |     |     |     |     | 735 |     |
| Val | Leu | Pro | Ala | Val | Glu | Arg | Ile | Leu | Arg | Ala | Phe | Gly | Tyr | Lys | Lys |
|     |     |     | 740 |     |     |     |     | 745 |     |     |     |     | 750 |     |     |
| Glu | Asp | Leu | Arg | Tyr | Gln | Lys | Thr | Arg | Gln | Val | Gly | Leu | Gly | Ala | Trp |
|     |     | 755 |     |     |     |     | 760 |     |     |     |     | 765 |     |     |     |
| Leu | Gly | Met | Gly | Gly | Glu | Arg | Leu | Lys | Leu |     |     |     |     |     |     |
| 770 |     |     |     |     | 775 |     |     |     |     |     |     |     |     |     |     |

( 2 ) INFORMATION FOR SEQ ID NO:5:

( i ) SEQUENCE CHARACTERISTICS:
      ( A ) LENGTH: 2337 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| ATGATCCTTG | ACGTTGATTA | CATCACAGAG | GACGGAAAGC | CCGTCATCAG | GGTCTTCAAG | 60 |
| AAGGATAAAG | GAGAGTTCAA | AATTGAGTAC | GACAGAGAAT | TCGAGCCCTA | CATCTATGCT | 120 |
| CTTCTCAGGG | ACGACTCTGC | CATCGAAGAA | ATCGAAAAGA | TAACTGCAGA | GAGGCACGGC | 180 |
| AAGGTCGTTA | AGGTTAAGCG | CGCGGAGAAG | GTGAAGAAAA | AGTTCCTCGG | CAGGTCTGTG | 240 |
| GAGGTCTGGG | TCCTCTACTT | CACGCACCCG | CAGGACGTTC | CGGCAATCCG | CGACAAAATA | 300 |
| AGGAAGCACC | CCGCGGTCAT | CGACATCTAC | GAGTACGACA | TACCCTTCGC | CAAGCGCTAC | 360 |
| CTCATAGACA | AGGGTCTCGT | CCCGATGGAG | GGCGATGAGG | AGCTTAAACT | CATGTCCTTC | 420 |
| GACATCGAGA | CGCTCTACCA | CGAGGGAGAA | GAGTTCGGAA | CCGGGCCGAT | TCTGATGATA | 480 |
| AGCTACGCAG | ATGAAAGCGA | GGCGCGTGTG | ATAACCTGGA | AGAAGATCGA | CCTGCCCTAC | 540 |
| GTCGACGTTG | TCTCCACCGA | GAAGGAGATG | ATAAAGCGCT | TCCTTAAGGT | CGTTAAGGAG | 600 |
| AAGGACCCGG | ACGTGCTGAT | AACATACAAC | GGCGACAACT | TCGACTTCGC | CTACCTCAAA | 660 |
| AAGCGGTGTG | AGAAGCTTGG | CGTGAGCTTT | ACCCTCGGCA | GGGACGGGAG | CGAGCCGAAG | 720 |
| ATACAGCGCA | TGGGCGACCG | CTTCGCCGTT | GAGGTGAAGG | GCAGGATCCA | CTTCGACCTG | 780 |
| TACCCCGTCA | TAAGGCGCAC | CATAAACCTC | CCGACCTACA | CCCTTGAGGC | TGTATACGAG | 840 |
| GCGGTTTTCG | GCAAGCCCAA | GGAGAAGGTC | TACGCCGAGG | AGATAGCCAC | CGCTTGGGAG | 900 |
| ACCGGCGAGG | GGCTTGAGAG | GGTCGCGCGC | TACTCGATGG | AGGACGCGAG | GGTTACCTAC | 960 |
| GAGCTTGGCA | GGGAGTTCTT | CCCGATGGAG | GCCCAGCTTT | CCAGGCTCAT | CGGCCAGGGT | 1020 |

| | | | | | | |
|---|---|---|---|---|---|---|
| CTCTGGGACG | TTTCCCGCTC | CAGCACCGGC | AACCTTGTTG | AGTGGTTTTT | GCTCAGGAAA | 1080 |
| GCCTACGAGA | GGAACGAACT | CGCTCCCAAC | AAGCCCGACG | AGAGGGAGCT | GGCGAGGAGA | 1140 |
| AGGGGGGGCT | ACGCCGGTGG | CTACGTCAAG | GAGCCGGAGC | GGGGACTGTG | GGATAATATT | 1200 |
| GTGTACCTCG | ATTTTCGCTC | GCTGTACCCC | TCCATTATCA | TCACCCACAA | CGTCTCGCCA | 1260 |
| GATACGCTCA | ACCGCGAGGG | ATGTAAGAGC | TACGACGTTG | CCCCGCAGGT | CGGTCACAAG | 1320 |
| TTCTGCAAAG | ACTTCCCCGG | CTTCATTCCG | AGCCTGCTCG | GAAACCTGCT | GGAGGAGAGG | 1380 |
| CAGAAGATAA | AGAGGAAGAT | GAAGGCAACG | CTCGACCCGC | TGGAGAGGAA | GCTTCTCGAT | 1440 |
| TATCGCCAGC | GCGCTATCAA | AATCCTGGCG | AACAGCTTCT | ACGGCTATTA | CGGCTACGCC | 1500 |
| AGGGCAAGAT | GGTACTGCAA | GGAGTGCGCC | GAGAGCGTTA | CGGCATGGGG | CAGGGAGTAC | 1560 |
| ATCGAAATGG | TTATCAGAGA | GCTTGAGGAA | AAGTTCGGTT | TTAAAGTCCT | CTATGCAGAC | 1620 |
| ACAGACGGTC | TTCATGCCAC | CATTCCTGGA | GCGGACGCTG | AAACAGTCAA | GAAAAAGGCA | 1680 |
| ATGGAGTTCT | TAAACTATAT | CAATCCCAAA | CTGCCCGGCC | TTCTCGAACT | CGAATACGAG | 1740 |
| GGCTTCTACG | TCAGGGGCTT | CTTCGTCACG | AAGAAGAAGT | ACGCGGTTAT | AGACGAGGAG | 1800 |
| GGCAAGATAA | CCACGCGCGG | GCTTGAGATA | GTTAGGAGGG | ACTGGAGCGA | GATAGCGAAG | 1860 |
| GAGACGCAGG | CGAGGGTTCT | TGAGGCGATA | CTCAGGCACG | GTGACGTTGA | GGAGGCCGTC | 1920 |
| AGAATCGTCA | AGGAAGTGAC | GGAAAAGCTG | AGCAAGTACG | AGGTTCCGCC | GGAGAAGCTG | 1980 |
| GTTATCCACG | AGCAGATAAC | GCGCGAGCTC | AAAGACTACA | AGGCCACCGG | CCCGCACGTG | 2040 |
| GCCATAGCGA | AGCGCCTCGC | CGCGAGGGGA | ATAAAGATAC | GCCCCGGGAC | GGTGATAAGC | 2100 |
| TACATCGTCC | TCAAGGGCTC | GGGGAGAATA | GGCGACAGGG | CCATTCCCTT | CGACGAGTTC | 2160 |
| GATCCGACGA | AGCACAGGTA | CGACGCTGAC | TACTACATCG | AGAACCAGGT | TCTTCCAGCG | 2220 |
| GTGGAGAGAA | TCCTCAGGGC | CTTCGGCTAC | AAGAAGGAAG | ACCTGCGCTA | CCAGAAGACG | 2280 |
| AGGCAGGTTG | GGCTTGGCGC | GTGGCTCGGA | ATGGGAGGAG | AAAGACTTAA | ACTTTAG | 2337 |

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:6:

AAGCACCCCG CGGTCA                                                        16

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:7:

TCCTTCGCCA TCGCGACGCT                                               20

( 2 ) INFORMATION FOR SEQ ID NO:8:

( i ) SEQUENCE CHARACTERISTICS:
        ( A ) LENGTH: 20 base pairs
        ( B ) TYPE: nucleic acid -continued (C) STRANDEDNESS: single
(D) TOPOLOGY: linear ( i i ) MOLECULE TYPE: Other Nucleic Acid ( x i ) SEQUENCE DESCRIPTION: SEQ ID NO:8:

AGCGTCGCGA TGGCGAAGGA 20

( 2 ) INFORMATION FOR SEQ ID NO:9:

( i ) SEQUENCE CHARACTERISTICS:
(A) LENGTH: 20 base pairs
(B) TYPE: nucleic acid
(C) STRANDEDNESS: single
(D) TOPOLOGY: linear ( i i ) MOLECULE TYPE: Other Nucleic Acid ( x i ) SEQUENCE DESCRIPTION: SEQ ID NO:9:

TCGAAGTGGA TCCTGCCCTT 20

THERMOCOCCUS BAROSSII DNA POLYMERASE MUTANTS

CROSS-REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

*Theriococcus barosii* is a thermophilic organism obtained from deep vent flange, Endeavor Segment, Juan de Fuca Ridge, off the coast of Washington State in the U.S.A. Native Tba (nTba) DNA polymerase has been purified from cell paste by classical chromatographic purification methods including Q-Sepharose, Heparin Sepharose, phosphocellulose and Mono-Q (U.S. Pat. No. 5,602,011). Characterization of the purified nTba showed that it possesses an active proofreading function in addition to its DNA-dependent DNA polymerase activity. Tba DNA polymerase does not possess detectable 5'-3' exonuclease activity. Because nTba DNA polymerase was obtained from a thermophilic organism, it was shown to retain polymerase activity following prolonged treatment at elevated temperatures (95° C.).

U.S. Pat. No. 5,602,011 discloses cloned Tba DNA polymerase.

Cloning of the gene for the Tba DNA polymerase DNA polymerase revealed that it is a member of the alpha-family of DNA polymerases and is approximately 80% conserved compared with the Pfu and Deep Vent DNA polymerases.

Based on amino acid sequence comparisons and protein expression studies on the truncated forms of other known polymerases, it can be shown that the organization of the gene is structured such that the 3'-5' exonuclease function is encoded in the 5' half of the gene, while the polymerase function is encoded in the latter half. The predicted amino acid sequence derived from the gene sequence highlights a metal binding site in the 3'-5' exonuclease domain. This domain is typified by the amino acid sequence FDIET and is conserved between Tba DNA polymerase, Pfu and Deep Vent. (See, for example, Vemori, et al., *Nucl. Acids Research* 21(2):259–265, 1993.)

Alteration of the FDIET sequence to FAIAT has been shown in some polymerases to eliminate the proofreading function. (Derbyshire, V., et al., *Science* 240:199–201, 1988; Bernad, A., et al., *Cell* 59:219–228, 1989; Frey, M. W., et al., *Proc. Natl. Acad. Sci. USA* 90:2579–2583, 1993; Mather, E. J., U.S. Pat. No. 5,489,523.)

BRIEF SUMMARY OF THE INVENTION

In one embodiment, the present invention is a *Thermococcus barosii* DNA polymerase with a reduced 3'-5' exonuclease activity. Preferably, the exonuclease activity is reduced at least 50% as measured by the ability of the polymerase to incorporate dNTPs into an oligonucleotide primer with mismatches. In a most preferable form of the invention, the reduction is at least 75% or 90%.

In one preferred form of the invention, the FDIET amino acid sequence (residues 140–144 of native Tba DNA polymerase) has been altered to FAIAT.

In another embodiment, the present invention is a polymerase with a reduced 3'-5' exonuclease activity wherein amino acid residue 489 has additionally been altered. In a preferred form of the present invention, residue 489 has been altered to either a tyrosine or a phenyalanine. In a most preferred form of the present invention, the residue is a tyrosine. In this embodiment, the polymerase has an increased ability to incorporate dideoxynucleotides and ribonucleotides compared to a Tba DNA polymerase with no alteration at residue 489. The ability to incorporate dideoxynucleotides is preferably at least 2-fold higher, and most preferably at least 3-fold higher than the unaltered Tba DNA polymerase. The ability to incorporate ribonucleotides is preferably at least 2-fold higher, more preferably at least 3-fold higher, and most preferably at least 5-fold higher than unaltered Tba DNA polymerase.

It is an object of the present invention to provide a DNA polymerase with increased utility for specific DNA polymerization applications that require a DNA polymerase with reduced exonuclease activity and increased ability to incorporate dideoxynucleotides and ribonucleotides. Most preferably, this DNA polymerization method is a method of arrayed primer extension.

It is another object of the present invention to provide a DNA polymerase with an altered residue 489.

Other objects, advantages, and features of the present invention will become apparent after one has reviewed the specification and claims.

DETAILED DESCRIPTION OF THE INVENTION

In one embodiment, the present invention is a *Thermococcus barosii* DNA polymerase with reduced 3'-5' exonuclease activity. In a preferred form of the polymerase, the polymerase also has an altered ability to incorporate dideoxy and ribonucleotides into a polymerization product.

By "Tba DNA polymerase" is meant a DNA polymerase corresponding to one naturally isolated from *Thermococcus barosii*. SEQ ID NO:4 is an amino acid sequence of one preferred form of Tba DNA polymerase. SEQ ID NO:5 is a nucleic acid sequence of a preferred Tba DNA polymerase.

The Examples below described one preferred method for obtaining the Tba DNA polymerase of the present invention. Briefly, the inventors have obtained a recombinant clone of Tba DNA polymerase. A recombinant clone can be obtained from the *T. barosii* strain deposited at DSM on Nov. 1, 1994 at Accession No. 9535. One would use standard methods of molecular biology to produce probes from SEQ ID NOs:4 and 5 capable of screening a genomic DNA preparation created from DSM 9535 or other Tba strain. These techniques could be used to create a recombinant clone suitable for producing a polymerase of the present invention. U.S. Pat. No. 5,602,011, hereby incorporated by reference, describes a preferred method of obtaining a polymerase clone.

The inventors used standard methods of site-directed mutagenesis to replace the amino acid residues FDIET (SEQ ID NO:1) with FAIAT (SEQ ID NO:2). (SEQ ID NO:1 occurs at residues 140–144 of the native Tba DNA polymerase sequence.) This particular alteration renders the polymerase deficient in 3'-5' exonuclease activity.

The Examples also disclose the alteration of residue 489 and the subsequent creation of a Tba DNA polymerase with altered ability to incorporate dideoxy and ribonucleotides. In the Examples below, the residue 489 was substituted with a tyrosine residue. We envision that a phenylalanine residue would be equally successful. We also envision that other amino acids could be substituted at residue 489 to create an equally successful polymerase. We envision that certain substitutions will provide a polymerase with greater ability to incorporate dideoxynucleotides and ribonucleotides than those described below.

A preferable DNA polymerase of the present invention has a reduced 3'-5' exonuclease activity that is reduced at least 50% as measured by the ability of the polymerase to incorporate dNTPs into an oligonucleotide primer with mismatches. The Examples below demonstrate this procedure. Preferably, the reduction is at least 75%. More preferably, the reduction is 90%.

In another embodiment, the DNA polymerase of the present invention has an increased ability to incorporate dideoxynucleotides as compared to Tba DNA polymerase with no alteration at residue 489. Preferably, this increase is at least 2-fold. More preferably, the increase is at least 3-fold. The increase can be measured by methods described below in the Examples.

In another embodiment, the Tba DNA polymerase of the present invention has an increased ability to incorporate ribonucleotides compared to Tba DNA polymerase with no substitute at residue 489. Preferably, the increase is at least 2-fold. More preferably, the increase is at least 3-fold and most preferably the increase is at least 5-fold.

In another embodiment, the present invention is a method of DNA polymerization comprising exposing the polymerase as described above to a DNA template, primer, dNTPs, and other reagents necessary for DNA polymerization. One particularly relevant DNA polymerization diagnostic application may be for an emerging "chip" technology referred to as Arrayed Primer Extension (APEX). In this method, DNA polymerases incorporate dye-terminators (eg. FL-ddNTPs) into bound oligonucleotide primers that are arrayed onto a solid support.

In one example, APEX technology is used to determine potential mutations in human DNA by amplifying a human target template gene sequence and exposing the sequence via APEX to a primer array. Upon successful hybridization and primer extension, the sequence of the template can be determined and potential mutations detected.

A Tba DNA polymerase mutant that prefers ddNTPs is useful in APEX for two reasons. First, template DNA samples may be generated by PCR from genomic DNA of human patients. Because the template preparation may be contaminated with free deoxynucleotides carried into the chip reaction, the deoxynucleotides may effectively compete away incorporation of the dideoxy terminators. A Tba DNA polymerase mutant may be isolated that prefers ddNTPs and also discriminates against dNTPs. This mutant polymerase would thereby eliminate this problem. Second, the Tba DNA polymerase mutant that better incorporates ddNTPs relative to the wild-type Tba DNA polymerase may enhance the overall sensitivity of the APEX reaction on the chip. The combination of these effects may be crucial to the overall sensitivity of the technique and thus drive success of using a primer extension reaction in chip-based technology.

EXAMPLES

A. Tba(exo-) DNA polymerase

Methods: Sequencing and site-directed modification of the rTba gene

The sequence of a recombinant clone of Tba DNA polymerase in pUC18 vector (called pUC18, rTba) was verified on both strands by automated DNA sequence analysis. (pUC18, rTba is described in U.S. Pat. No. 5,602,011) CY5-labeled oligonucleotide primers that would hybridize throughout the presumed Tba DNA polymerase coding sequence were synthesized and purified utilizing C18 syringe cartridges. Dideoxy-sequencing reactions with T7 DNA polymerase were carried out in microwell dishes with approximately 5–10 μg of purified pUC18, rTba plasmid DNA according to manufacturer's specifications (AutoRead Sequencing Kit, Pharmacia Biotech, Uppsala, Sweden) and electrophoresed using the ALFexpress automated DNA sequencing apparatus (Pharmacia Biotech). DNA sequence comparisons were made using DNASTAR alignment software (DNASTAR, Inc., Madison, Wis.).

The recombinant Tba DNA polymerase coding region was cloned into the pET22b vector (Novagen, Madison, Wis.) to enable expression in bacteria to be driven from the bacteriophage T7 promoter. The 2.1 kb NdeI-XmaI and 275 bp XmaI-EcoRI fragments that span the full-length rTba coding region were isolated from pUC18, rTba and ligated into pET22b that was previously digested with NdeI and EcoRI and then dephosphorylated with calf intestinal phosphatase (Pharmacia Biotech). The correct construct was isolated by restriction endonuclease mapping and the sequence at the cloning junctions verified by automated DNA sequence analysis.

DNA resequencing identified a one bp deletion in the Tba DNA polymerase coding region that deviated from the sequence originally reported in U.S. Pat. No. 5,602,011. A deletion of "A" occurs normally where GAG would encode glutamic acid at amino acid residue number 666 and results in the stop codon TAA to be aligned in-frame two codon positions downstream of the defect. To repair the defective gene, an oligonucleotide primer (repair primer 1) was synthesized that would hybridize to the sense region of interest and enable insertion of "A" in one round of PCR when used in conjunction with an antisense vector oligonucleotide. Another oligonucleotide (repair primer 2) was synthesized that includes a 5' BlpI restriction endonuclease site to extend the round one product and enable a BlpI-BlpI replacement fragment to be inserted into the Tba DNA polymerase coding region. The restored sequence encodes a full-length recombinant Tba DNA polymerase in pET22b (termed p22b, rTbaFL).

A rTba(exo-) expression vector was constructed using overlapping PCR mutagenesis to introduce alanines (A) in place of aspartic (D) and glutamic (E) acid in a metal binding site (FDIET, SEQ ID NO:1) located within the presumed 3'-5' exonuclease domain. "FDIETI" is located at residues 140–144. Two mutagenic primers encoding E. coli-preferred codons were used in round one of PCR to generate DNA fragments that overlap at the corresponding FAIAT, SEQ ID NO:2, sequence. (These primers are listed at SEQ ID NOs:6–9. SEQ ID NOs:6 and 7 are the 5' set. SEQ ID NOs: 8 and 9 are the 3' set.) A mixture of these fragments in a PCR reaction, with a sense primer located 5' to the SacII site and an antisense primer positioned 3' to the BamHI site, amplified a Tba DNA polymerase fragment containing FAIAT in place of FDIET. Following restriction endonuclease digestion, the SacII-BamHI mutagenic fragment was cloned in place of the normal Tba DNA polymerase sequence to create vector p22b, rTba(exo-).

All large scale plasmid DNA preparations were obtained from 350 ml E. coli cultures grown overnight at 37° C. in 2×YT+100 μg/ml ampicillin medium (Molecular Cloning, A Laboratory Manual, second edition) by using Qiagen Tip-500 columns (Qiagen, Chatsworth, Calif.). Small mini-DNA preparations were grown in 2–5 ml of 2×YT+ampicillin medium overnight and purified using GFX reagents (Pharmacia Biotech). The integrity of each clone was validated by automated sequence analysis for any manipulated region of the Tba DNA polymerase coding region. Restriction endonucleases and T4 DNA ligase were from either Pharmacia Biotech (Milwaukee, Wis.) or New England Biolabs (Beverly, Mass.). Taq DNA polymerase was from Perkin-Elmer (Perkin-Elmer Corp., Foster City, Calif. 94404) with PCR reactions completed in a Perkin-Elmer thermocycler for 30 cycles with a 1 minute denaturation step at 940° C., 1 minute annealing step at 50° C. and a 0.5–1 minute extension step at 72° C. All oligonucleotide primers were manufactured and purified at Pharmacia Biotech. Electrocompetent XL1-blue cells were obtained from Stratagene (La Jolla, Calif.) for cloning purposes.

Expression of the rTba gene

For expression of the different forms of recombinant Tba DNA polymerase, a portion of the mini-preparation of vector DNA from the XL1-blue cloning step was transferred into heat-shock competent BL21(DE3) cells (Stratagene) and transformant cells selected on LB+ ampicillin medium. To evaluate expression of rTbas, 50 ml of 2×YT+ampicillin medium was inoculated with at least 10 colonies from either the transformant plate or a plate culture originating from at least 10 colonies. Following log-phase growth to O.D. 0.8–1.2 at 600 nm, cells were induced for recombinant protein production with 1 mM final IPTG for 3 hours at 37° C. The induced cultures were centrifuged at 4000 rpm in a IEC Centra-7 equipped with a fixed-angle rotor (International Equipment Company, USA) for 15 minutes at 4° C. The cell paste was immediately frozen at −20° C. to preserve intact recombinant proteins until lysates were prepared.

For lysate preparation, the cell paste was resuspended at twice the cell weight in TMN buffer (50 mM Tris-HCl, pH 8.5, 10 mM magnesium chloride, 16 mM ammonium sulfate) with 500 μg/ml lysozyme and incubated for 15 minutes with occasional mixing. The resuspension was made 0.1% with Triton X-100 and Tween 20, freeze-thawed 2 times at −80° C., then made 1 mM final with PMSF. Following microcentrifugation at top speed, the supernatant which contains the recombinant Tba DNA polymerase was filtered through a 0.2 micron syringe filter and stored at 4° C.

Purification of the rTba(exo−)

BL21(DE3) cells transformed with p22b, rTba(exo−) were grown to log phase in a 15 L fermentation run containing terrific broth (Molecular Cloning, A Laboratory Manual, second edition) and 100 μg/ml ampicillin. Cells were induced with 1 mM IPTG for 3 hours and the cell paste collected and frozen at −20° C. 60 g of the cell paste was diluted with 180 ml of lysis buffer (50 mM Tris-HCl, pH 8.0, 1 mM EDTA, 1 mM DTT, 1 mM PMSF and 0.2 mg/ml lysozyme), sonicated, then centrifuged for 30 minutes at 10K rpm at 4° C. in a Beckman centrifuge equipped with a JA-10 rotor. The supernatant containing soluble recombinant protein was heated to 80° C. for 20 minutes to denature contaminating E. coli proteins, then cooled to 4° C. To remove the contaminating DNA, the supernatant was made 0.6% final with polyethylenimine (PEI, Sigma), stirred on ice for 30 minutes and followed by centrifugation at 10k, 30 minutes, 4° C. The supernatant containing the semi-purified rTba(exo−) was stored at 4° C.

To further purify the rTba(exo−), 160 ml of the PEI supernatant was passed onto a Q-Sepharose anion exchange resin (Pharmacia) previously equilibrated against 50 mM Tris-HCl, pH 8.0, 1 mM EDTA, 1 mM PMSF, 1 mM DTT and the bound rTba(exo−) eluted using a 0–1M KCl gradient. Approximately 20 μl of the Q-Sepharose column fractions were evaluated by using either Silver (Bio Rad) or Coomassie Blue staining of the protein in SDS-PAGE under reducing conditions. A Q-Sepharose pool was collected based on visualization of the fractions containing the most rTba(exo−) in the absence of contaminating E. coli proteins. This pool was dialyzed versus buffer A (50 mM Tris-HCl, pH 8.5, 20 mM ammonium sulfate, 0.1 mM EDTA, 1.0 mM DTT, 10% glycerol and 0.1% Tween 20) and passed over Heparin Sepharose CL-6B resin (Pharmacia). After washing with buffer A to return to baseline, the rTba(exo−) was eluted with a 20–300 mM ammonium sulfate gradient in buffer A. The best fractions were evaluated as described above for the Q-Sepharose Fast Flow column and combined to yield a 1.5 L pool. The final rTba(exo−) preparation was obtained by stir-cell concentrating the Heparin pooled fractions to approximately 120 ml and dialyzing into storage buffer (50% glycerol, 50 mM ammonium sulfate, 20 mM Tris-HCl, pH 8.5, 0.1 mM EDTA, 1 mM DTT, 0.5% NP40, 0.5% Tween 20).

Physical characterization of native Tba DNA polymerase and rTba(exo−)

A semi-purified preparation of native Tba DNA polymerase was electrophoresed by SDS-PAGE then immunoblotted in CAPS buffer (10 mM, pH 11) to nitrocellulose. The membrane was stained with imido black and the approximately 90 kD band corresponding to native Tba DNA polymerase excised from the membrane and delivered to the Protein-Nucleic Acid Shared Facility at the Medical College of Wisconsin for N-terminal sequence evaluation. The N-terminal sequence and the amino acid composition of rTba(exo−) was determined in a similar fashion except that the material used was obtained directly from the pooled Heparin column and dialyzed into phosphate buffer (20 mM potassium phosphate, pH 7.5, 0.5 mM sodium EDTA, 50 mM potassium chloride, 1 mM DTT, 5% glycerol, 0.1% NP-40, 0.1% Tw20)

Biochemical characterization of recombinant Tba DNA polymerase Proteins

Contaminating nickase and endonuclease levels were evaluated for purified preparations. The nickase levels are determined using phiX-174 RFI DNA as the substrate. Samples are electrophoresed on a 1% agarose gel in Tris-Acetate buffer to separate supercoiled DNA (Form I), covalently closed circular DNA (Form II) and linear DNA (Form III). The standard assay conditions are: 10 mM Tris-HCl (pH 8.3), 2 mM magnesium chloride, 50 mM potassium chloride, 0.01% gelatin and 66.6 μg/ml φX174 DNA in 30 μl at 65° C. for 1 hour.

To detect contaminating endonuclease activity in the polymerase samples, lambda DNA is used as a substrate under the following assay conditions: 1× OPA buffer (Pharmacia Biotech), 10 mM Tris acetate, pH 7.5, 10 mM magnesium acetate and 50 mM potassium acetate plus 20 μg/ml lambda DNA in a 50 μl reaction at 65° C. for 16 hours. These digested samples are electrophoresed on 1% agarose gels to look for digestion of the lambda DNA.

The ability of DNA polymerases to incorporate dNTPs into an oligonucleotide primer reflects one activity of the enzyme. The standard M13/primer assay conditions are as follows: 25 mM glycine (pH 9.3), 50 mM potassium chloride, 2 mM magnesium chloride, 1 mM DTT, 20 μg/ml M13mpl8(+) DNA, 6 μg/ml single stranded primer, 0.2 mM dTTP, dCTP and dGTP, 0.1 mM [α-$^{32}$P]-dATP (5 μCi/ml) and 100 μg/ml BSA in a 50 μl reaction at 70° C. for 10 minutes. Several dilutions of recombinant polymerases or those in lysate preparations are typically assayed to insure that the conditions reflect the linear range of the enzyme.

For analysis of the polymerases to incorporate FL-or CY5 labeled-ddNTPs in the APEX format, different dilutions of each enzyme preparation were tested in the following format.

For oligonucleotide binding to Covalink microwell plates (Nunc, Naperville, Ill.), ~20 ng/rxn of primer oligonucleotide was heat treated at 100° C. for 3 minutes, then placed on ice for 5 minutes. The oligonucleotide was diluted to 0.25 ng/μl with 10 mM 1-methylimidazole, pH 7.0, and 75 μl added to each well. 25 μl of 200 mM 1-ethyl-3-(3-dimethylaminopropyl)-carbodiimide was added to each well, the wells covered with 96-well tape and incubated at 50° C. overnight. Following incubation, the wells were washed 3× with immunowash (0.25% SDS or Tween 20, 0.4N NaOH) and rinsed one time with either 1× PBS or ddH$_2$O. These wells are now compatible for APEX reactions taking place in an incubator format.

An individual APEX reaction typically consists of 0.25–1.0 ng/μl template, 0.5–1.0 μg thermostable DNA polymerase, 1 μM dye-ddNTP, 1 μM ddNTP mix (lacking the dye-ddNTP chosen) diluted to a total volume of 100 μl (Covalink plates) or 50 μl (Nucleolink plates) with TSP buffer (10 mM potassium chloride, 20 mM Tris-HCl, pH 8.0, 10 mM ammonium sulfate, 2 mM magnesium sulfate, 0.1% Triton X-100). (For a general description of APEX, see Shumaker, J. M., et al., *Human Mutation* 7:346–354, 1996.) After sealing the wells with tape, the reaction for the Covalink plates takes place in a 72° C. oven for 30 minutes.

APEX reactions are evaluated using an antibody/colorimetric detection system. Following completion of the APEX reaction, the plates are washed 3–4× with 150 of 1× PBS. Open sites on the microwells are blocked with 3% BSA in 1× PBS for 30 minutes at room temperature. Anti-CY5 or anti-FL antibody (1:500 dilutions in 3% BSA solution) is next added for 60 minutes and the plates washed 3–4× with 150 μl of 1×PBS containing 0.05% Tween 20. After rinsing with 1× PBS or ddH$_2$O, 100 μl of p-nitrophenylphospate (PNPP) is added and the color allowed to develop at room temperature on the bench. Optical density is measured with an endpoint ELISA Spectromax Pro software package at 405 nm in a Spectromax 250 microwell plate spectrophotometer (Molecular Devices).

Table 1, below, tabulates the results of experiments analyzing the APEX activity of rTba (exo$^-$) during classical purification.

TABLE 1

| DNA polymerase | APEX activity (OD @ 405 nm) (A) | A/wt[a] |
|---|---|---|
| rTba(exo), lysate | 0.12 | 0.2 |
| rTba(exo), Q-Sepharose | 0.18 | 1.5 |
| rTba(exo), Heparin | 0.42 | 1.6 |
| rTba(exo), Heparin, storage | 0.34 | 1.4 |

[a]$A_{405nm}$ measurements were normalized to the mass of protein used in the assay.

Results

A Tba DNA polymerase clone was sequenced on both strands and found to encode a potential DNA polymerase. The cloned gene contains a 1 bp deletion near the 3' end of the molecule that would result in premature truncation and a truncated version of recombinant Tba DNA polymerase. This site was repaired based on the homology to Deep Vent and Pfu amino acid sequence and both the defective and repaired gene expressed via a T7 promoter system in bacteria. The recombinant Tba DNA polymerase from the repaired gene was expressed at high levels and at the appropriate size when compared to the native Tba DNA polymerase by SDS-PAGE analysis of heat-treated bacterial lysates. As predicted, the defective gene resulted in a shorter form. Examination of the recombinant polymerases' ability to incorporate dNTPs was demonstrated either by using a nonradioactive DNA polymerase assay (Boehringer Mannheim) or an M13/primer incorporation assay (see Methods). These analyses showed that the full-length recombinant Tba DNA polymerase, but not the carboxy-truncated form, is an active DNA dependent DNA polymerase at high temperatures.

While the normal recombinant Tba DNA polymerase was able to incorporate dNTPs in the above assay formats, to date we have been unable to demonstrate that it is capable of functioning in the arrayed-primer extension format. Because early experiments showed that commercially-available Deep Vent (New England Biolabs, Beverly, Mass.) does not incorporate ddNTPs in APEX, but Deep Vent(exo$^-$) (New England Biolabs) does, we proposed that APEX requires polymerase activity in the absence of the 3'-5' exonuclease activity. In most chip technologies primers are in the 3'-5' orientation and are not substrates for 3'-5' exonucleases. The orientation of our primers, however, is 5'-3'. Therefore, we decided an exo$^-$ enzyme is necessary because use of exo$^+$ enzymes in normal primer extension applications and PCR can often be problematic. Thus, there may be an advantaged in using an exo- polymerase in APEX, in addition to other applications. With that in mind, a recombinant form of Tba DNA polymerase was engineered where the FDIET sequence in the exonuclease domain is altered to FAIAT (termed "rTba (exo$^-$) ").

To determine whether rTba (exo$^-$) exhibited a decrease in proofreading activity, an exonuclease assay was performed that is based on having a mispaired 3' end of a primer oligonucleotide when hybridized to the template strand (in this case M13 DNA). This type of assay relies on the ability of the enzyme's proofreading function to excise the mispaired 3' sequence, thereby allowing the polymerase function to incorporate radioactively labeled dNTPs. As Table 2 illustrates, all of the polymerases tested are able to effectively incorporate the labeled DATP as long as there is a perfect match between the 3' end of the primer and the template. However, only native Tba DNA polymerase and wild-type Deep Vent displayed the ability to excise the 3 or 6 bases of mispaired nucleotides to enable subsequent polymerization. Thus, the FDIET to FAIAT alterations significantly diminished 3'-5' exonuclease activity in the recombinant Tba DNA polymerase, especially when comparing the native form to the exonuclease-deficient Tba DNA polymerase.

TABLE 2

Elimination of proofreading exonuclease in recombinant Tba DNA polymerase

| DNA polymerase | perfect homology (cpm incorporated) | 3 bp mismatch[a] % of perfect match | 6 bp mismatch[a] % of perfect match |
|---|---|---|---|
| native Tba DNA polymerase | 14,658 | 75 | 69 |
| rTba(exo) | 12,119 | 5 | 2 |
| Deep Vent | 11,587 | 99 | 70 |
| Deep Vent(exo) | 8,540 | 9 | 6 |
| AmpliTaq | 15,522 | 9 | 8 |

[a]Primers with a mismatched 3' terminus were annealed to single-stranded M13 DNA. Polymerase activity (cpms incorporated) is possible only if exonuclease activity is present to first excise the mismatched bases. Under our conditions, extension is not possible off a mismatched primer terminus.

The ability of rTba(exo$^-$) to function in the APEX format was tested with material purified by Q-Sepharose and Heparin chromatography (see Table 1). In the APEX format, the primer oligonucleotide is bound to a microwell support where it hybridizes with a template oligonucleotide in an orientation compatible with the ability of a polymerase to incorporate nucleotides. Unlike purified native Tba DNA polymerase, the rTba(exo$^-$) is able to incorporate FL-ddATP in the primer extension format. From the relative APEX activities per weight of enzyme added (see column 4, Table 1, A/wt), it appears that rTba(exo⁻) is inhibited when in a lysate preparation as compared to the more purified forms (i.e. Q-Separose, Heparin). In addition, using the defined assay conditions (see Methods), it appears that purified KlenTaq with a mutation at 667 (Taquenase, Wayne M. Barnes, Washington University, School of Medicine, St. Louis, Mo. 63110) performs about many times better than either Deep Vent(exo⁻) or rTba(exo⁻) in the APEX format.

Having the purified versions of both native and recombinant Tba DNA polymerase at hand enabled us to determine that the N-terminal sequence was intact and agreed with the sequence predicted from the cloned Tba DNA polymerase gene.

B. Tba (exo⁻) DNA polymerase mutants

Methods: In general

The purpose of the experimentals below is to design variations of the thermostable recombinant DNA polymerase described above originating from *Thermococcus barosii* that are exonuclease deficient and have altered nucleotide substrate specificities.

As described above, the rTba DNA polymerase gene was made exonuclease deficient by changing the aspartate and glutamate residues in the FDIET consensus region to alanines as described above. This rTba(exo–) gene was then mutated in the KILANSFY (SEQ ID NO:3) (aa 487–494) consensus region.

Site-directed mutagenesis (U.S.E. mutagenesis kit, Pharmacia Biotech or Deng, et al., *Anal. Biochem.* 200, 81C, 1992) was performed as described above, such that the I, L, A, N, S, and F residues were changed to tyrosines (Y). Table 3, below, lists these mutations.

To effectively assess their activities in the APEX reaction, the mutants were purified from the crude heat-treated lysate. This was accomplished by cloning a His-Tag sequence onto the C-terminus of the mutant genes and purifying by metal-chelation chromatography. The amount of His-tagged protein isolated was quantified by ELISA.

A summary of the mutants' activities in APEX reactions are described below in Table 3. Briefly, the APEX reactions were performed in a microwell system in which a primer was fixed to the solid surface via its phosphate at the 5' end. A template sequence oligo, buffer, nucleotides, enzyme and fluorescently-labeled nucleotide (deoxy- , dideoxy- , or ribonucleotide) were introduced into the well. The reactions were incubated at 72° C. for 30 minutes, and the wells washed to terminate the reactions. Detection of incorporated Fl-(d,dd, or r)NTP was accomplished by incubating with anti-fluorescein Ab conjugated to alkaline phosphatase, adding p-nitrophenyl phospate (pNPP) substrate and reading the optical density at 405 nm.

Three isolated clones of each mutant were tested in triplicate at two enzyme concentrations to insure linearity of the assay with respect to enzyme activity. The average activity (normalized to amount of rTba protein in the assay) for each mutant is shown in Table 3.

Conclusions

Activities of the I, L, A, N, and F tyrosine mutants can be compared to that of rTba(exo–)/His DNA polymerase. The ability of each of the mutants to incorporate deoxynucleotides is not significantly altered by the mutants except for the N491Y mutant in which this activity is decreased 3–4-fold. All mutants were assayed for their ability to incorporate a dideoxy terminator and ribonucleotides. Of interest is the dideoxy activity of the L489Y/His mutant which is approximately 3-fold greater than that of the exo–/His enzyme. This mutant also displays enhanced ability to incorporate ribonucleotides as well.

It is evident that the perturbation at the L489 residue has an effect on nucleotide substrate specificity and is a key residue involved in this function.

TABLE 3

KILANSFY "Tyrosine" Mutant Activities

| | Deoxy Activity/ ng (×1000) | Dideoxy Activity/ ng (×1000) | Ribo Activity/ ng (×1000) | Dideoxy: Deoxy | Ribo: Deoxy |
|---|---|---|---|---|---|
| Exo/His | 13.0 | 1.2 | 0.4 | 0.09 | 0.03 |
| I488Y/His | 14.1 | 0.2 | 0.1 | 0.01 | 0.01 |
| L489Y/His | 10.5 | 3.5 | 2.1 | 0.33 | 0.20 |
| A490Y/His | 13.6 | 0.6 | 0.2 | 0.04 | 0.01 |
| N491Y/His | 3.5 | 0.1 | 0.0 | 0.03 | — |
| F493Y/His | 16.6 | 1.7 | 0.6 | 0.10 | 0.04 |

---

We claim:

1. A mutant of a native *Thermococcus barossii* DNA polymerase wherein the mutant polymerase has reduced 3'–5' exonuclease activity relative to the native polymerase, wherein the mutant polymerase comprises SEQ ID NO:2, wherein the mutant polymerase further comprises a different amino acid residue 489 than the native polymerase, and wherein the mutant polymerase also has increased ability to incorporate dideoxy nucleotides or ribonucleotides relative to the native polymerase.

2. The polymerase of claim 1 wherein amino acid residue 489 is selected from the group consisting of tyrosine and phenylalanine.

3. The polymerase of claim 2 wherein residue 489 is a tyrosine.

4. The polymerase of claim 1 wherein the increase is at least 2-fold.

5. The polymerase of claim 4 wherein the increase is at least 3-fold.

6. The polymerase of claim 1 wherein the increase is at least 5-fold.

7. A method of DNA polymerization, comprising reaching the polymerase of claim 8 with a DNA template, primer, dNTPs, and other reagents necessary for polymerization.

8. A method of arrayed primer extension, comprising the steps of
 a. exposing the polymerase of claim 1 to bound oligonucleotide primers that are arrayed on a solid support, chain terminators, and to other reagents necessary for primer extension, and
 b. incorporating chain terminators, whereby primer extension ceases.

* * * * *